United States Patent
Moshe et al.

(10) Patent No.: US 11,964,455 B2
(45) Date of Patent: Apr. 23, 2024

(54) BREATHABLE ELASTIC LAMINATES FOR WEARABLE ARTICLES AND METHODS FOR MAKING SAME

(71) Applicant: FITESA FILM PRODUCTS LLC, Simpsonville, SC (US)

(72) Inventors: Amir Moshe, N. Chesterfield, VA (US); David L Godshall, N. Chesterfield, VA (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 528 days.

(21) Appl. No.: 16/941,014

(22) Filed: Jul. 28, 2020

(65) Prior Publication Data

US 2021/0101377 A1    Apr. 8, 2021

Related U.S. Application Data

(60) Provisional application No. 62/910,755, filed on Oct. 4, 2019.

(51) Int. Cl.
  *B32B 27/12*    (2006.01)
  *A61F 13/15*    (2006.01)
  *B32B 3/10*     (2006.01)
  *B32B 3/26*     (2006.01)
  *B32B 5/02*     (2006.01)
  *B32B 7/12*     (2006.01)
  (Continued)

(52) U.S. Cl.
  CPC ........ *B32B 27/12* (2013.01); *A61F 13/15707* (2013.01); *B32B 3/10* (2013.01);
  (Continued)

(58) Field of Classification Search
  CPC ..... B32B 27/12; B32B 3/266; B32B 2307/51; B32B 2307/724; B32B 2555/02; A61F 13/49009; A61F 2013/15552
  See application file for complete search history.

(56) References Cited

U.S. PATENT DOCUMENTS 4,655,760 A * 4/1987 Morman ............... A61F 13/514
                                                      604/385.26
4,834,741 A * 5/1989 Sabee ............... A61F 13/49009
                                                      604/385.29
(Continued)

FOREIGN PATENT DOCUMENTS

WO    WO-2016099549 A1 * 6/2016 ........... B32B 25/042

OTHER PUBLICATIONS

International Search Report and Written Opinion dated Nov. 13, 2020, for International Patent Application No. PCT/US2020/051168.

(Continued)

*Primary Examiner* — Jasper Saberi
(74) *Attorney, Agent, or Firm* — KARCESKI IP LAW, PLLC

(57) ABSTRACT

A method for manufacturing a breathable elastic laminate includes aperturing an elastic film to create an apertured elastic film with a pattern. The pattern includes a plurality of first lanes extending in a machine direction, each of the plurality of first lanes having a plurality of apertures, and a plurality of second lanes extending in the machine direction. Each of the plurality of second lanes is devoid of apertures and has a width of at least twice the width of one of the apertures in the first lanes. The plurality of second lanes alternate with the plurality of first lanes in a cross direction substantially orthogonal to the machine direction. The method includes stretching the apertured elastic film in the machine direction to activate the apertured elastic film and bonding a first side of the activated apertured elastic film to a nonwoven web to create a breathable elastic laminate.

25 Claims, 16 Drawing Sheets

(51) Int. Cl.
    *B32B 27/16*     (2006.01)
    *B32B 37/00*     (2006.01)
    *B32B 37/12*     (2006.01)
    *A61F 13/49*     (2006.01)

(52) U.S. Cl.
    CPC .............. *B32B 3/266* (2013.01); *B32B 5/022* (2013.01); *B32B 7/12* (2013.01); *B32B 27/16* (2013.01); *B32B 37/0084* (2013.01); *B32B 37/12* (2013.01); *A61F 2013/15552* (2013.01); *A61F 2013/1591* (2013.01); *A61F 2013/49022* (2013.01); *B32B 2250/40* (2013.01); *B32B 2274/00* (2013.01); *B32B 2307/51* (2013.01); *B32B 2307/718* (2013.01); *B32B 2307/72* (2013.01); *B32B 2307/724* (2013.01); *B32B 2555/02* (2013.01)

(56) References Cited

U.S. PATENT DOCUMENTS

| | | | |
|---|---|---|---|
| 5,284,703 A * | 2/1994 | Everhart | D04H 1/492 |
| | | | 428/326 |
| 6,537,930 B1 | 3/2003 | Middlesworth et al. | |
| 7,087,289 B2 | 8/2006 | Soon et al. | |
| D637,008 S | 5/2011 | Frost | |
| 8,377,027 B2 | 2/2013 | Hughes et al. | |
| 9,011,625 B2 | 4/2015 | Siqueira et al. | |
| 9,821,542 B2 | 11/2017 | Bruce et al. | |
| 10,226,908 B2 | 3/2019 | Palzewicz et al. | |
| 2006/0251858 A1 | 11/2006 | Thomas et al. | |
| 2007/0141303 A1 | 6/2007 | Steindorf | |
| 2007/0144660 A1 | 6/2007 | O'Sickey et al. | |
| 2011/0119850 A1 | 5/2011 | Mallory et al. | |
| 2012/0271265 A1 | 10/2012 | Langdon | |
| 2017/0297313 A1* | 10/2017 | Langford | B32B 25/10 |
| 2017/0326832 A1* | 11/2017 | Palzewicz | B32B 27/302 |
| 2018/0126618 A1 | 5/2018 | Middlesworth et al. | |

OTHER PUBLICATIONS

Indian Office Action dated Jul. 27, 2022, for Indian Patent Application No. 202217019546.

International Preliminary Report on Patentability dated Apr. 14, 2022, for International Patent Application No. PCT/US2020/051168.

Brazilian Office Action dated Oct. 17, 2023, for Brazilian Patent Application No. 112022006469-1.

\* cited by examiner

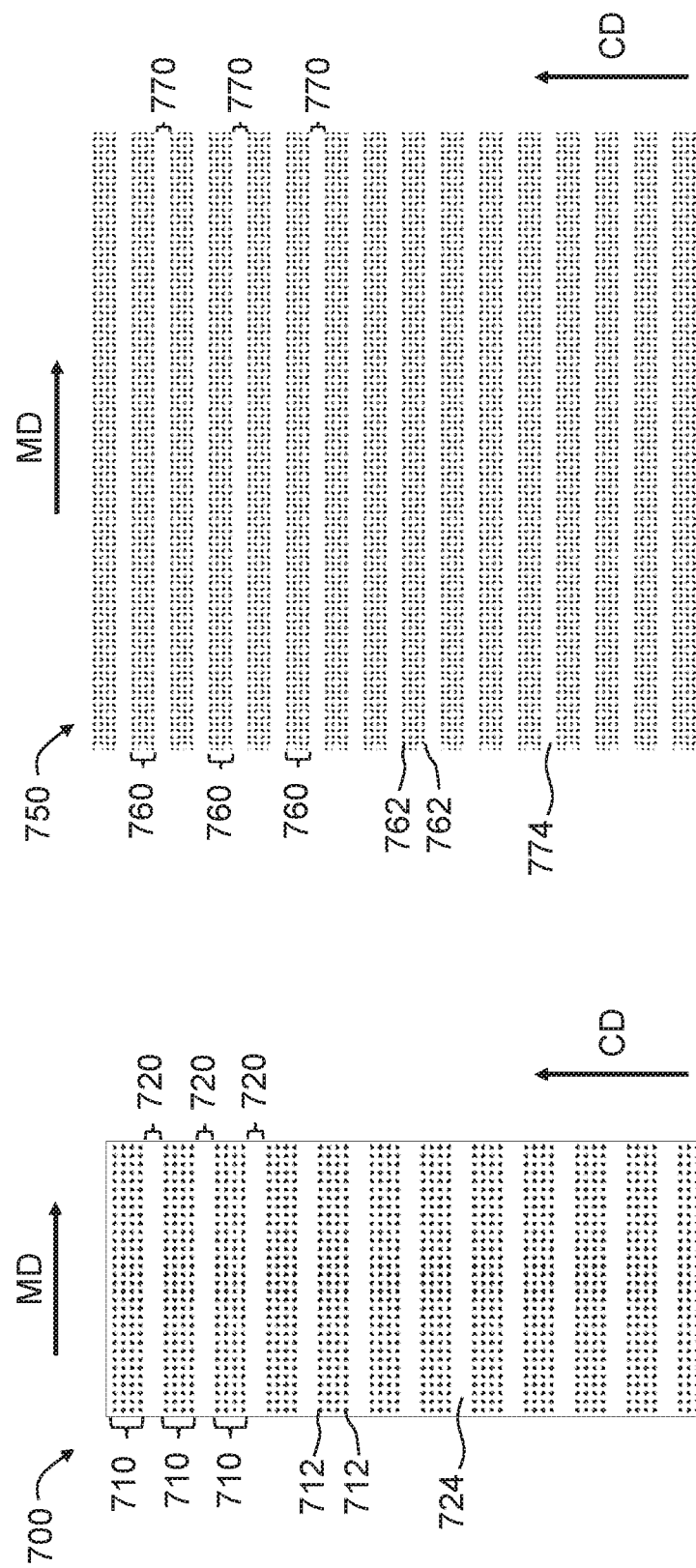

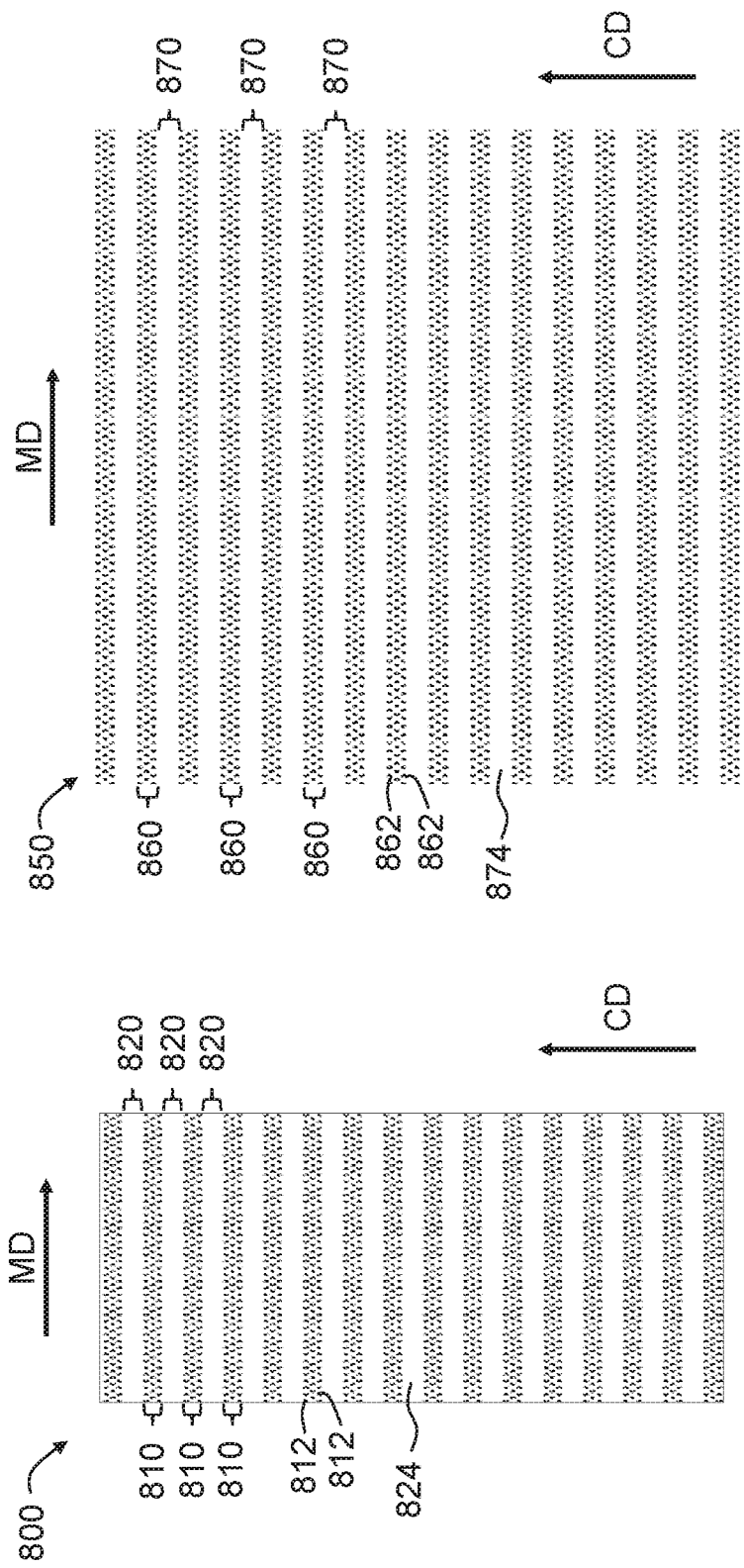

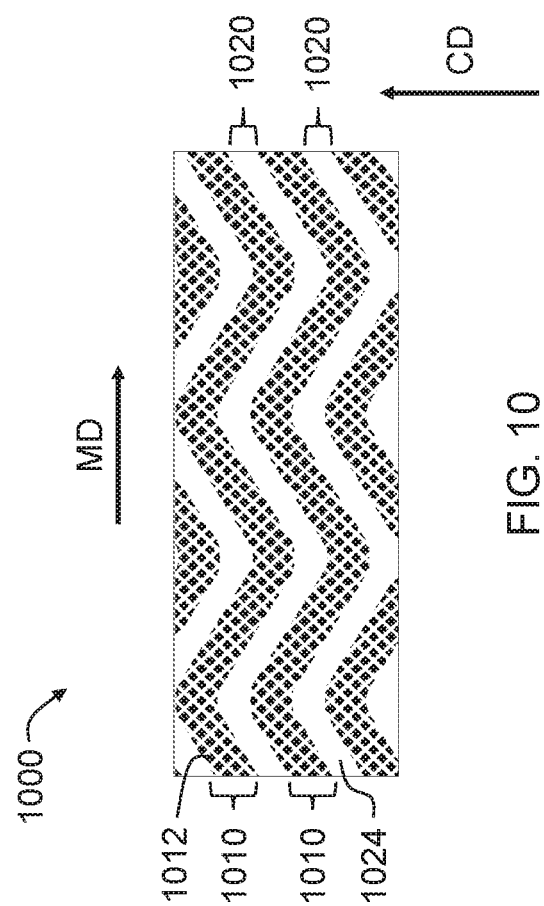
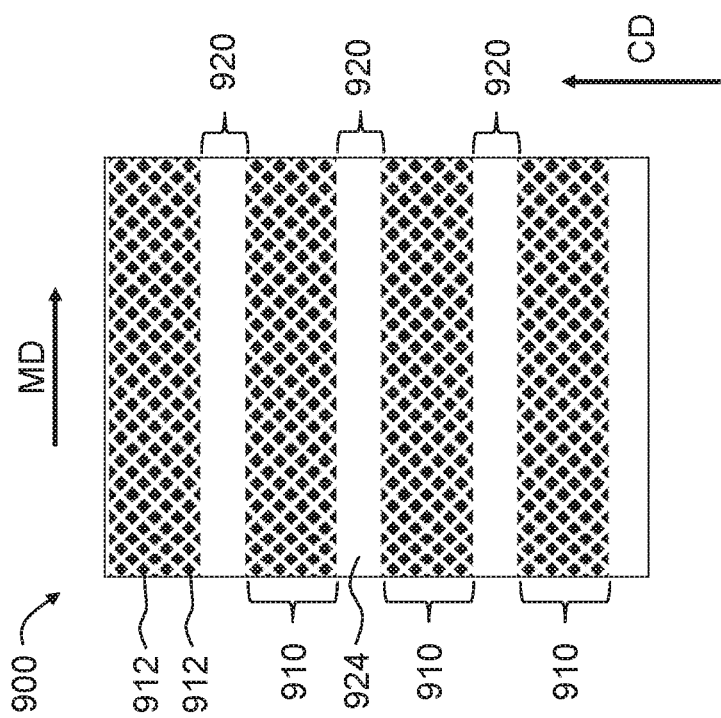

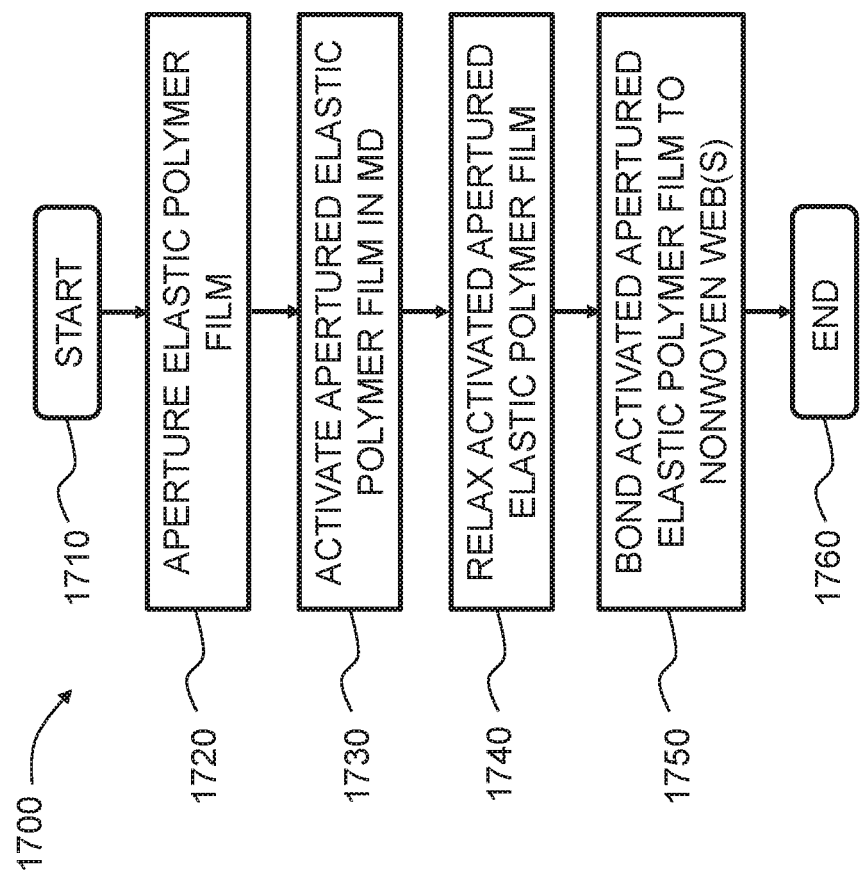

BREATHABLE ELASTIC LAMINATES FOR WEARABLE ARTICLES AND METHODS FOR MAKING SAME

CROSS-REFERENCE TO RELATED APPLICATIONS

This application relies for priority on and claims the benefit of priority to U.S. Provisional Patent Application Ser. No. 62/910,755, filed Oct. 4, 2019, the entire content of which is hereby incorporated by reference.

FIELD

The present invention relates to breathable elastic laminates that may be incorporated into wearable articles, such as absorbent articles, and methods for making the breathable elastic laminates.

BACKGROUND

Elastic laminates are used in the manufacture of many goods, including wearable articles, such as garments, hats, gowns, coveralls, absorbent articles, etc., and are typically used to provide desired fit characteristics to the article. In particular, elastic laminates that are used in the manufacture of absorbent articles, such as diapers, training pants, adult incontinence articles, and similar articles help provide a close, comfortable fit about the wearer. Many conventional absorbent articles employ elastic materials in the waist and/or torso sections of the article in order to secure the article around a wearer. Absorbent articles may also employ various elastic portions, such as leg cuffs, side tabs, side ears, and side panels. It may be desirable for the elastic laminate to be breathable to provide additional comfort for the wearer.

Many breathable elastic laminates known in the art include elastic strands, such as strands of LYCRA® brand elastomer, to provide elasticity to the article. In the manufacture of elastic strand laminates, the strands are placed under tension and adhesively laminated to at least one, and typically two nonwoven fibrous webs. The nonwoven webs provide a cloth like texture to the laminate. The elastic strands are then allowed to relax, causing the nonwoven bonded to the strands to gather and pucker to a greater extent than the nonwoven not bonded to the strands, resulting in a bulky appearance. The larger the spacing between the strands, the more undesirable bulky, puckered appearance. In some applications, such as training pants and adult incontinence articles, the bulky appearance is objectionable. In order to make the resulting laminate smoother and less bulky, the number of elastic strands used should be increased approximately three-fold. The increased number of elastic strands adds to the cost of the laminate, and also results in significantly more complicated and less robust manufacturing process. For example, the increased number of strands may become difficult to manage and, if any of the strands break, the process may be stopped for a considerable period of time while the strand(s) are re-threaded into the machine.

It is desirable to have a more robust breathable elastic laminate that does not include elastic strands.

SUMMARY

According to an aspect of embodiments of the invention, there is provided a method for manufacturing a breathable elastic laminate. The method includes aperturing an elastic film to create an apertured elastic film with a pattern. The pattern includes a plurality of first lanes extending in a machine direction, each of the plurality of first lanes including a plurality of apertures, and a plurality of second lanes extending in the machine direction. Each of the plurality of second lanes is devoid of apertures and has a width greater than twice the width of one of the plurality of apertures in the first lanes. The plurality of second lanes alternate with the plurality of first lanes in a cross direction substantially orthogonal to the machine direction. The method includes stretching the apertured elastic film in the machine direction to activate the apertured elastic film in the machine direction, and bonding a first side of the activated apertured elastic film with the activated apertured elastic film under tension to a nonwoven web to create a breathable elastic laminate.

In an embodiment, the method includes relaxing the activated apertured elastic film prior to bonding. In an embodiment, the activated apertured elastic film is relaxed at least 5%. In an embodiment, the activated apertured elastic film is relaxed between 5% and 70%. In an embodiment, the activated apertured elastic film is relaxed between 10% and 40%.

In an embodiment, the elastic film is apertured using an apertured forming structure and a vacuum.

In an embodiment, the plurality of apertures are three-dimensional apertures.

In an embodiment, the method includes activating the apertured elastic film in the cross direction prior to stretching the apertured elastic film in the machine direction.

In an embodiment, the bonding includes sonic bonding.

In an embodiment, the bonding includes applying an adhesive to the apertured elastic film or the nonwoven web.

In an embodiment, the method includes bonding a second side of the apertured elastic film, opposite the first side, to a second nonwoven web.

In an embodiment, the apertured elastic film is stretched up to 400% in the machine direction.

According to an aspect of the invention, there is provided a breathable elastic laminate that includes an apertured elastic film layer having a pattern. The pattern includes a plurality of first lanes extending in a machine direction, each of the plurality of first lanes including a plurality of apertures, and a plurality of second lanes extending in the machine direction. Each of the plurality of second lanes is devoid of apertures and has a width at least twice the width of one of the plurality of apertures in the first lanes. The plurality of second lanes alternate with the plurality of first lanes in a cross direction substantially orthogonal to the machine direction. A nonwoven layer is attached to a first surface of the apertured elastic film layer.

In an embodiment, the plurality of apertures are three-dimensional apertures.

In an embodiment, a second nonwoven layer is attached to a second surface of the elastic film layer, opposite the first surface.

In an embodiment, the breathable elastic laminate has an air permeability between about 0.1 $m^3/m^2$/minute and about 150 $m^3/m^2$/minute. In an embodiment, the breathable elastic laminate has an air permeability between about 10 $m^3/m^2$/minute and about 50 $m^3/m^2$/minute.

In an embodiment, the apertured film layer has a basis weight between about 5 gsm and about 50 gsm. In an embodiment, the apertured film layer has a basis weight between about 25 gsm and about 40 gsm.

In an embodiment, the nonwoven layer includes a nonwoven material having a basis weight between about 10 gsm and about 50 gsm. In an embodiment, the nonwoven material has a basis weight between about 20 gsm and about 40 gsm.

In an embodiment, the nonwoven layer includes a nonwoven material selected from the group consisting of a spunbond nonwoven material, a spunlace nonwoven material, a spunbond-meltblown-spunbond ("SMS") nonwoven material, and a spunbond-meltblown-meltblown-spunbond ("SMMS") nonwoven material.

In an embodiment, the plurality of first lanes and the plurality of second lanes are generally straight.

In an embodiment, the plurality of first lanes and the plurality of second lanes are wavy.

According to an aspect of embodiments, of the invention, there is provided an absorbent article that includes the breathable elastic laminate according to any one of the embodiments described herein.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale, although at least one embodiment of the invention illustrated in the figures and described herein may be drawn to scale. Reference characters designating corresponding components are repeated as necessary throughout the figures for the sake of consistency and clarity.

FIG. 7A is a schematic illustration of a portion of an embodiment of a forming structure of the apparatus of FIG. 5;

FIG. 7B is a schematic illustration of a portion of an embodiment of an apertured elastic film made with the forming structure of FIG. 7A;

FIG. 8A is a schematic illustration of a portion of another embodiment of the forming structure of the apparatus of FIG. 5;

FIG. 8B is a schematic illustration of a portion of an embodiment of an apertured elastic film made with the forming structure of FIG. 8A;

FIG. 9 is a schematic illustration of a portion of another embodiment of the forming structure of the apparatus of FIG. 5;

FIG. 10 is a schematic illustration of a portion of another embodiment of the forming structure of the apparatus of FIG. 5;

FIG. 17 is a flowchart illustrating a method for making a breathable elastic laminate, according to embodiments of the invention;

DETAILED DESCRIPTION

Figure 1:
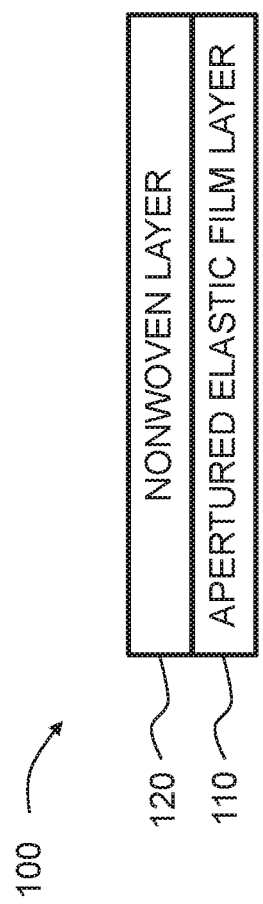
FIG. 1 is a schematic illustration of a breathable elastic laminate having an apertured elastic film layer and a nonwoven layer attached to one side of the apertured elastic film layer, according to embodiments of the invention.

The term "web" as used herein refers to a material capable of being wound into a roll. Webs can be film webs, nonwoven webs, laminate webs, apertured laminate webs, etc. The face of a web refers to one of its two-dimensional surfaces, as opposed to its edge. The term "composite web" refers to a web that comprises two or more separate component webs that are attached to each other in a face to face relationship. Each of the separate component webs does not have to be continuous across the entire composite web and can have discontinuous parts. The attachment can be through the edges of the component webs, or the attachment can be at particular locations across the component webs, or the attachment can be continuous across the faces of the component webs.

The term "film" as used herein refers to a web made by extruding a molten sheet of thermoplastic polymeric material by a cast or blown extrusion process and then cooling the sheet to form a solid polymeric web. Films can be monolayer films, coextruded films, coated films, and composite films. Coated films are films comprising a monolayer or coextruded film that are subsequently coated (for example, extrusion coated, impression coated, printed, or the like)

with a thin layer of the same or different material to which it is bonded. "Composite films" are films comprising layers of more than one component film and the component films are combined in a bonding process. Each of the separate component films does not have to be continuous across the entire composite film and can have discontinuous parts. Bonding processes may incorporate adhesive layers between the film layers.

The term "apertured film" as used herein denotes a film in which there exists a plurality of apertures that extend from one surface to a second surface. The apertures may be two-dimensional apertures that connect the second surface of a flat film to the first surface of the film and in which no three-dimensional structure exists. The apertures may be three-dimensional apertures that have a three-dimensional structures, such as protuberances, extending from one side of the film and apertures through the three-dimensional structures (e.g., the apertures have a depth that is thicker than the thickness of the film). Non-limiting examples of three-dimensional structures include cones, funnels, volcanoes, and the like, whether circular or not.

The term "breathable film" or "breathable laminate" as used herein means a film or laminate that has an air permeability of greater than 0.1 meters$^3$/meters$^2$/minute (m$^3$/m$^2$/min) when measured in a device such as a Textest FX3300 Air Permeability Tester.

The term "nonwoven" as used herein means a material comprising a plurality of fibers. The fibers may be bonded to each other or may be unbonded. The fibers may be staple fibers or continuous fibers. The staple fibers may be thermal bonded carded fibers or air through bonded carded fibers. The continuous fibers may be meltblown fibers, spunlace fibers, spunbond fibers and the like, as well as combinations thereof. The fibers may comprise a single material or may comprise a multitude of materials, either as a combination of different fibers, or as a combination of similar fibers each comprised of different materials. As used herein, "nonwoven web" is used in its generic sense to define a nonwoven having a generally planar structure that is relatively flat, flexible and porous. The nonwoven web may be the product of any process for forming the same and may include a composite or combination of webs, such as, for example, a spunbond-meltblown-spunbond ("SMS") nonwoven web.

The term "elastic" or "elastomeric" as used herein refers to a material having at least 80% recovery from 50% elongation. The term "inelastic" as used herein refers to a material that does not exhibit 80% recovery once elongated 50%. Inelastic materials may exhibit some level of elasticity but break or are permanently damaged when stretched beyond 50% elongation. As an example only, recovery testing may be performed by stretching a sample that is 1 inch wide with a gauge length of 2 inches to a "test elongation" at 20 inches/minute, held for 30 seconds, allowed to relax at 20 inches/minute to 0% extension, held for 60 seconds, and then stretched at 20 inches/minute. The "permanent set" is the elongation of the sample at which the load cell first detects a load in excess of 1 Newton on the second extension. The "percent recovery" is calculated as 100×(test elongation−permanent set)/test elongation. For example, when a length of material that was 10 inches in length in a normal resting state not under tension is elongated 50%, it is stretched by 5 inches to 15 inches in length. The material is then released and permitted to return to a resting state. If the length of the material at which the load cell first detects a load in excess of 1 Newton on the second extension is 11 inches or less, it is considered to have at least 80% recovery.

The term "absorbent article" as used herein denotes articles that absorb and contain fluids and other exudates. Absorbent articles include garments that are placed against or in proximity to the body of a wearer to absorb and contain the various exudates discharged from a body. A non-exhaustive list of examples includes absorbent towels, diapers, training pants, absorbent underpants, adult incontinence products, feminine hygiene products and the like.

The term "activating" or "activation" as used herein refers to a process of stretching a material beyond a point where its physical properties are changed. In the case of a nonwoven web, sufficient activation of the web will result in the nonwoven web being more extensible and/or improving its tactile properties. In an activation process, forces are applied to a material causing the material to stretch. Both films and nonwoven webs may be mechanically activated, for example. Mechanical activation processes comprise the use of a machine or apparatus to apply forces to the web to cause stretching of the web. Methods and apparatus used for activating webs of materials include, but are not limited to, activating the web through intermeshing gears or plates, activating the web through incremental stretching, activating the web by ring rolling, activating the web by tenter frame stretching, canted wheel stretchers or bow rollers, and activating the web in the machine direction between nips or roll stacks operating at different speeds to mechanically stretch the web, and combinations thereof.

The term "point bonding" as used herein refers to bonding two or more layers of material at a plurality of discrete points. For example, thermal point bonding generally involves passing two or more layers of material to be bonded between heated rolls, for example, an engraved pattern roll and a smooth calendar roll. The engraved roll is patterned in some way so that the entire fabric is not bonded over its entire surface, and the calendar roll is usually smooth. As a result, various patterns for engraved rolls have been developed for functional as well as aesthetic reasons.

The term "sonic bonding" as used herein refers to a point bonding process performed, for example, by passing materials to be bonded together between a sonic horn and an anvil roll such as is known in the art. In an exemplary method of ultrasonic bonding, the various layers that are to be attached together are simultaneously fed to the bonding nip of an ultrasonic unit. In general, the unit produces high frequency vibration energy that melts the thermoplastic within the layers at distinct bond sites and joins the layers together. The amount of induced energy, speed by which the combined components pass through the nip, gap at the nip, as well as the number of bond sites determine the extent of adhesion between the various layers. Very high frequencies are obtainable, and frequencies in excess of 18,000 cps (cycles per second) are usually referred to as "ultrasonic". Depending on the desired adhesion between various layers and the choice of materials to be bonded, frequencies as low as 5,000 cps, or even lower, may produce an acceptable product.

Various embodiments of the present invention will now be highlighted. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

FIG. 1 schematically illustrates a breathable elastic laminate 100 in accordance with embodiments of the invention. As illustrated, the breathable elastic laminate 100 is a so-called "bi-laminate" having an apertured elastic film layer 110 attached to a nonwoven layer 120 on one side thereof. The apertured elastic film layer 110 may be continuous across the entire breathable elastic laminate 100, or may be discontinuous in one or more directions and located in sections or strips of the breathable elastic laminate 100. The nonwoven layer 120 may be continuous across the entire breathable elastic laminate 100 or may be discontinuous in one or more directions and located in sections or strips of the breathable elastic laminate 100. Additional aspects of embodiments of the breathable elastic laminate 100 will be described in further detail below.

Figure 2:
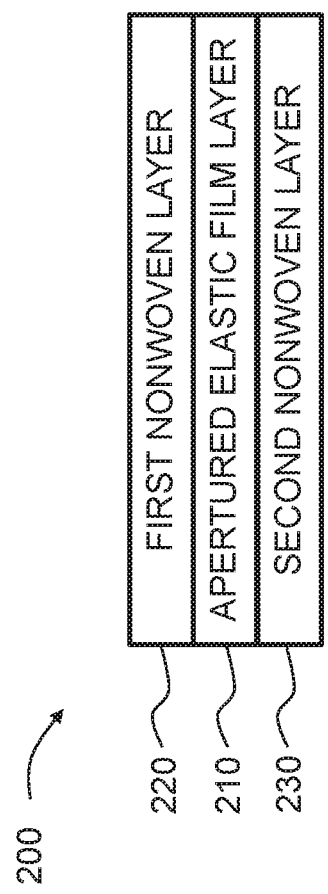
FIG. 2 is a schematic illustration of a breathable elastic laminate having an apertured elastic film layer and a nonwoven layer attached to each side of the apertured elastic film layer, according to embodiments of the invention.

FIG. 2 schematically illustrates a breathable elastic laminate 200 in accordance with embodiments of the invention. As illustrated, the breathable elastic laminate 200 is a so-called "tri-laminate" having an apertured elastic film layer 210, a first nonwoven layer 220 on one side of the apertured elastic film layer 210, and a second nonwoven layer 230 on an opposite side of the apertured elastic film layer 210 as the first nonwoven layer 220. Additional aspects of embodiments of the breathable elastic laminate 200 will be described in further detail below.

Figure 3:
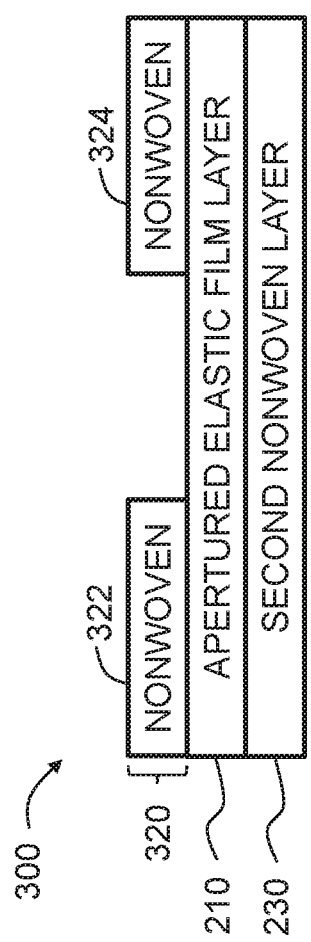
FIG. 3 is a schematic illustration of a breathable elastic laminate having two portions configured as tri-laminates and a single portion configured as a bi-laminate, according to embodiments of the invention.

FIG. 3 schematically illustrates a breathable elastic laminate 300 in accordance with embodiments of the invention. As illustrated, the breathable elastic laminate 300 is similar to the breathable elastic laminate web 200 illustrated in FIG. 2 and has the apertured elastic film layer 210 and the second nonwoven layer 230 on one side of the apertured elastic film layer 210, but instead of having the continuous first nonwoven layer 220 on the opposite side of the apertured elastic film layer 210 as the second nonwoven layer 230, the breathable elastic laminate 300 has a first nonwoven layer 320 that includes separate sections of nonwoven material 322, 324. Such a configuration provides a tri-laminate at the locations of the sections of nonwoven material 322, 324 and a bi-laminate in between the locations of the sections of nonwoven material 322, 324.

The illustrated embodiments of the breathable elastic laminate 100, 200, 300 are not intended to be limiting in any way, and other configurations of a breathable elastic laminate are contemplated as being with the scope of embodiments of the inventions. For example, in an embodiment, the apertured elastic film layer 110, 210 may be discontinuous and include separate sections of apertured elastic film across the nonwoven layer(s) 120, 220, 230, 320.

Each nonwoven layer 120, 220, 230, 320 may be made from any suitable nonwoven material that includes fibrous materials, such as staple fiber materials including thermal bonded carded fibers and air through bonded carded fibers, continuous fiber materials including meltblown fibers, spunlace fibers, spunbond fibers, and the like, as well as combinations thereof. In an embodiment, the nonwoven material may have a spunbond-meltblown-spunbond ("SMS") construction or a spunbond-meltblown-meltblown-spunbond ("SMMS") construction. The fibers within the nonwoven material may be made of polyethylene (PE), polypropylene (PP), bicomponent or blends of PE and PP, or other materials, such as polyethylene terephthalate (PET). In an embodiment, the fibers may include natural fibers, such as cotton and/or cellulose. Additionally, the nonwoven material may be homogeneous or contain a variety of materials including bicomponent fibers (e.g., having an inner core of one material and an outer core of a second material), and fibers of different morphologies, geometries, and surface finishes.

The basis weight of the nonwoven material in the nonwoven layer 120, 220, 230, 320 may be in the range of about 5 grams per square meter ("gsm") to about 100 gsm. In an embodiment, the basis weight of the nonwoven material in the nonwoven layer 120, 220, 230, 320 may be in the range of about 10 gsm and about 50 gsm. In an embodiment, the basis weight of the nonwoven material in the nonwoven layer 120, 220, 230, 320 may be in the range of about 20 gsm to about 40 gsm.

Figure 4:
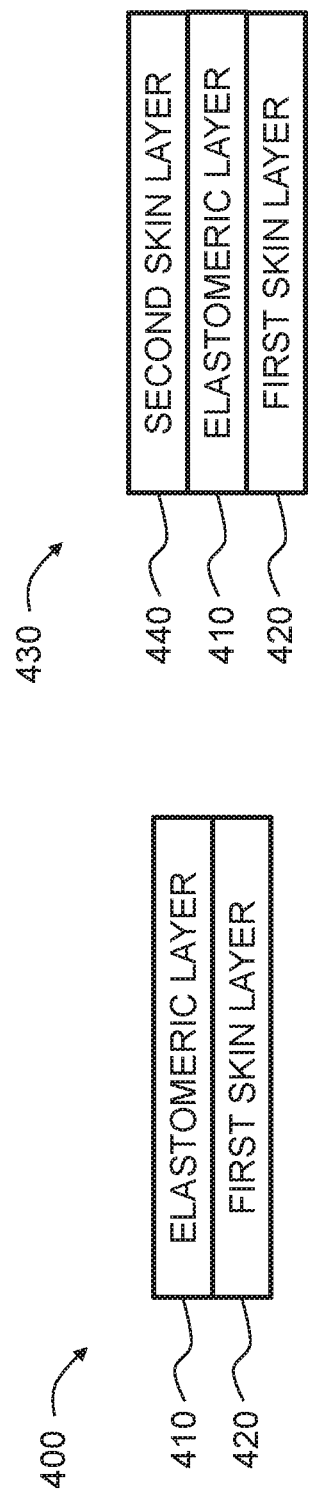
FIG. 4A is a schematic illustration of an embodiment of the apertured elastic film layer of FIGS. 1, 2 and 3.
FIG. 4B is a schematic illustration of an embodiment of the apertured elastic film layer of FIGS. 1, 2 and 3.

FIG. 4A schematically illustrates an embodiment of an apertured elastic film 400 that may be used as the apertured elastic film layers 110, 210 of the breathable elastic laminates 100, 200, 300 of FIGS. 1-3. The apertured elastic film 400 includes an elastomeric material layer 410 and a first skin layer 420 on one side thereof. In an embodiment, the apertured elastic film 400 may also include a second skin layer on an opposite side of the elastomeric material layer 410 as the first skin layer 420. For example, FIG. 4B schematically illustrates an embodiment of an apertured elastic film 430 that may be used as the apertured elastic film layers 110, 210. The apertured elastic film 430 includes the elastomeric material layer 410, the first skin layer 420 on one side of the elastomeric material layer 410, and a second skin layer 440 on an opposite side of the elastomeric material layer 410 as the first skin layer 420.

The illustrated embodiments are not intended to be limiting in any way. For example, in an embodiment, the apertured elastic film may not have any skin layers and may only be made from the elastomeric layer 410. In an embodiment, additional layers may be used to make the apertured elastic film, such as additional elastomeric layers and/or additional skin layers and/or additional layers in between the elastomeric material layer 410 and the skin layers 420, 440. In an embodiment, the apertured elastic film 400, 430 may include a plurality of two-dimensional apertures and/or a plurality of three-dimensional apertures, as described in further detail below.

The elastomeric material layer 410 may be made from any suitable elastic material, such as natural or synthetic polymeric materials. Examples of suitable polymeric materials include low crystallinity polyethylene, metallocene catalyzed low crystallinity polyethylene, polyolefin based elastomers such as INFUSE™ olefin block copolymers manufactured by Dow Chemical Company, VISTAMAXX™ performance polymers manufactured by Exxon Mobil Corporation, and the like, ethylene vinyl acetate copolymers ("EVA"), polyurethane, polyisoprene, butadiene-styrene copolymers, styrene block copolymers such as styrene/isoprene/styrene ("SIS"), styrene/butadiene/styrene ("SBS"), styrene/ethylene-butadiene/styrene ("SEBS"), or styrene/ethylene-propylene/styrene ("SEPS") block copolymers. Blends of these polymers alone or with other modifying elastic or non-elastomeric materials may also be used. For example, the elastomeric material layer 410 may be made from blends of styrene block copolymers with polyolefins, such as polyethylene or polypropylene, polyolefin-based elastomers, and/or any combination thereof, or any other suitable elastic material.

Each skin layer 420, 440 may include a suitable material that is more or less elastic than the elastomeric material layer 410. In an embodiment, each skin layer 420, 440 may include one or more polyolefins, such as polyethylene or polypropylene. The skin layers 420, 440 and/or the elastomeric material layer 410 may also include additives, such as colorants, processing aids, deodorants, surfactants, etc., as are known in the art.

The basis weight of the apertured elastic film 400, 430 may be in the range of about 5 grams per square meter ("gsm") to about 200 gsm. In an embodiment, the basis weight of the apertured elastic film 400, 430 may be in the range of about 10 gsm and about 50 gsm. In an embodiment, the basis weight of the apertured elastic film layer 400, 430 may be in the range of about 20 gsm and about 40 gsm.

The air permeability of the apertured elastic film 400, 430 may be in the range of about 0.1 $m^3/m^2/min$ to about 150 $m^3/m^2/min$ when measured in a device such as a Textest FX3300 Air Permeability Tester. In an embodiment, the air permeability of the apertured elastic film 400, 430 may be in the range of about 10 $m^3/m^2/min$ and about 50 $m^3/m^2/min$.

The apertured elastic film 400, 430 may have an elongation at break of at least about 50%. In an embodiment, the apertured elastic film 400, 430 may have an elongation at break of at least 100%. In an embodiment, the apertured elastic film 400, 430 may have an elongation at break of at least about 400%.

Figure 5:
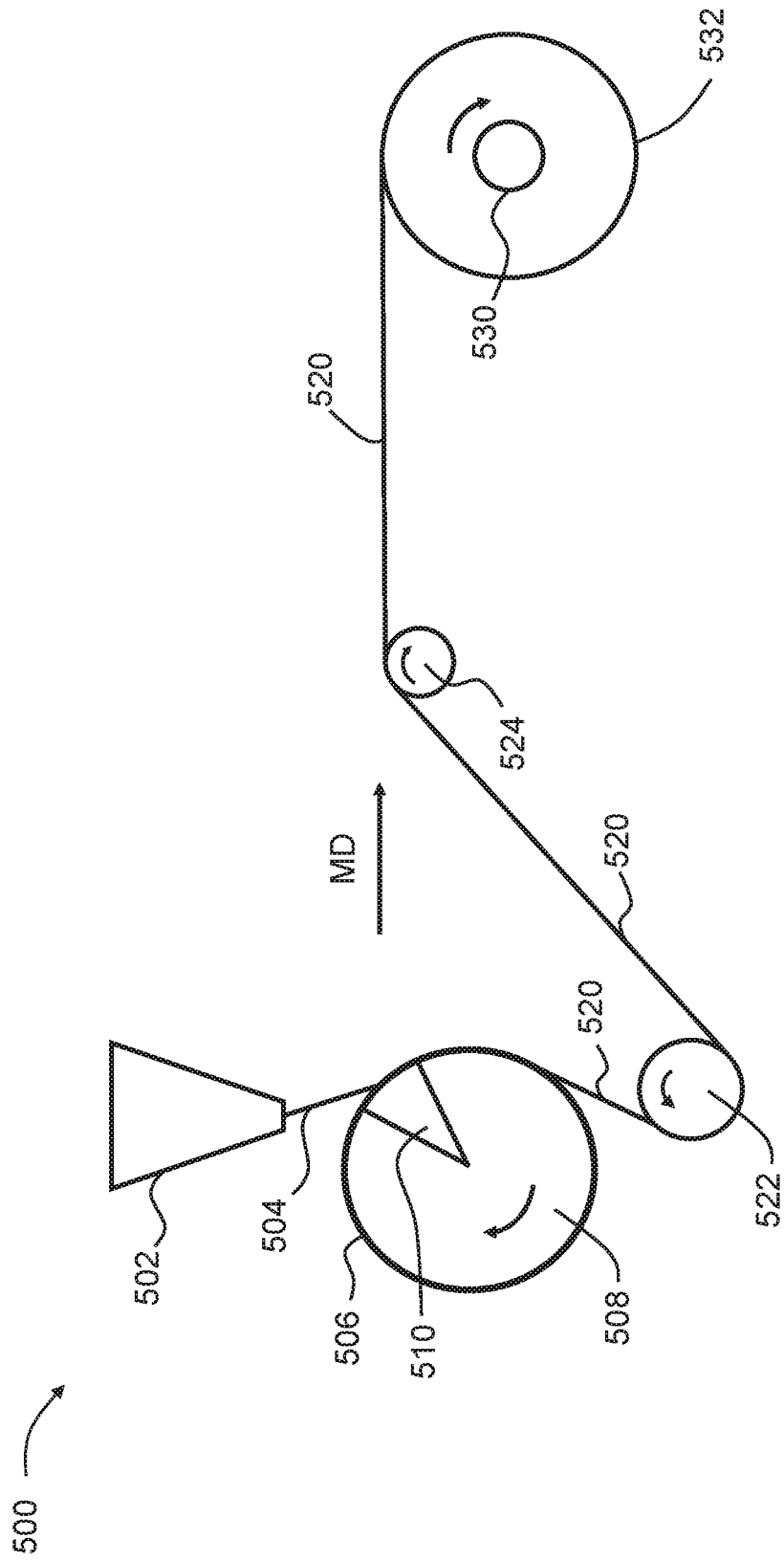
FIG. 5 is a schematic illustration of an apparatus for manufacturing an apertured elastic film for the breathable elastic laminate of FIGS. 1-3, according to embodiments of the invention.

FIG. 5 schematically illustrates an apparatus 500 that may be used to manufacture the apertured elastic film 400, 430 that may be used as the apertured elastic film layer 110, 210 for the breathable elastic laminates 100, 200, 300 of embodiments of the invention described herein. As illustrated, an extrusion die 502 extrudes a polymer melt curtain 504 onto a cylindrical forming structure 506 that includes a pattern of apertures and rotates about a cylinder 508 that has a vacuum slot 510 through which a vacuum is pulled. The polymer melt curtain 504 may include, for example, one or more of the materials described above with respect to the elastomeric material layer and the skin layers, as well as one or more additives, including, for example, colorants, processing aids, etc.

The polymer melt curtain 504 begins to solidify into an elastic web 520 when the polymer melt curtain 504 contacts the forming structure 506. As the elastic web 520 crosses over the vacuum slot 510, portions of the elastic web 520 are pulled into the apertures of the forming structure 506 by the vacuum such that a plurality of three-dimensional apertured protuberances are formed in the elastic web 520 in substantially the same pattern of apertures in the forming structure 506. Examples of the forming structure 506 according to embodiments of the invention are discussed in further detail below. As the elastic web 520 is apertured, air flow is initiated through the three-dimensional apertured protuberances, which cools and solidifies the three-dimensional apertured protuberances. The elastic web 520 is also cooled by the forming structure 506 between the three-dimensional apertured protuberances. The resulting apertured elastic web 520 is pulled off of forming structure 506 by a peel roller 522 and travels in a machine direction MD to one or more subsequent rollers 524 until it may be wound by a winder 530 into a roll 532. Additional rollers and/or other pieces of equipment may be used in the apparatus 500. The illustrated embodiment is not intended to be limiting in any way.

Figure 6:
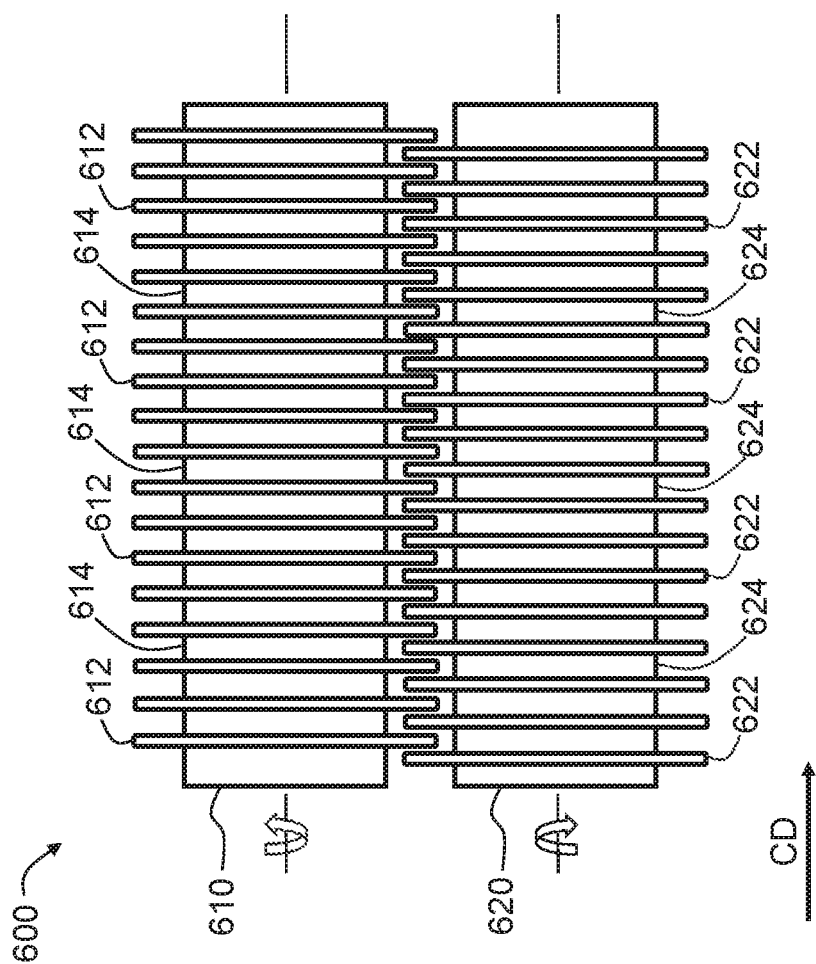
FIG. 6 is a schematic illustration of an optional activation station that may be used in the apparatus of FIG. 5, according to an embodiment of the invention.

For example, in an embodiment, the apparatus 500 may also include additional equipment between the roller 524 and the winder 530, such as an activation station 600, which is schematically illustrated in FIG. 6. As illustrated, the activation station 600 includes a first intermeshing gear ("IMG") roller 610 and a second intermeshing gear ("IMG") roller 620 that may be used to activate the apertured elastic web 520 in a transverse or cross direction CD that is orthogonal to the machine direction MD, if desired. The IMG rollers 610, 620 have their axes of rotation disposed in parallel relationship in the cross direction CD. The first IMG roller 610 includes a plurality of axially-spaced, side-by-side, circumferentially-extending, equally-configured gears 612 that can be in the form of thin fins having a generally rectangular cross section. The second IMG roller 620 includes a plurality of axially-spaced, side-by-side, circumferentially-extending, equally-configured gears 622 that can be in the form of thin fins having a generally rectangular cross section. The plurality of gears 612 of the first IMG roller 610 complement the plurality of gears 622 of the second IMG roller 620.

The spaces between adjacent gears 612, 622 define recessed, circumferentially-extending, equally configured grooves 614, 624 respectively. The grooves 614, 624 may have a generally rectangular cross section when the gears 612, 622 have a generally rectangular cross section. Desirably, the grooves 614, 624 have a larger width than that of the gears 612, 622 to permit the apertured elastic web 520 that passes between the IMG rollers 610, 620 to be received within the respective grooves 614, 624 and locally stretched. The spacing and the depth of engagement of the gears 612, 622 determines the degree of elongation to which the apertured elastic web 520 is subjected, as understood by one of ordinary skill in the art.

Other equipment that may be included in the apparatus 500 include, but are not limited to, a corona treatment apparatus, printers, festooning equipment, spooling equipment, and additional processing equipment that may emboss or provide additional apertures to the apertured elastic web 520.

Although the illustrated apparatus 500 is a vacuum forming apparatus, other types of apparatus may be used to aperture the elastic web. For example, in an embodiment, a hydroforming apparatus that uses a liquid, such as water, to force the elastic web into apertures of a forming structures and form three-dimensional apertures in the elastic web may be used. In an embodiment, a pin punching unit that includes pins or needles may be used to aperture the elastic web.

FIG. 7A is a schematic illustration of a portion of a forming structure 700, which may be used as the forming structure 506 of the apparatus 500 of FIG. 5, according to an embodiment of the invention. As illustrated, the forming structure 700 has a pattern that includes a plurality of first lanes 710 that alternate with a plurality of second lanes 720 in the cross direction CD and extend in the machine direction MD around the circumference of the forming structure 700. In the illustrated embodiment, the plurality of first lanes 710 and the plurality of second lanes 720 are generally straight. In an embodiment, the plurality of first lanes 710 and the plurality of second lanes 720 may be wavy, similar to a pattern described below with respect to FIG. 10. Each of the plurality of first lanes 710 includes a plurality of apertures 712 that extend through the forming structure 700. As illustrated, the apertures 712 are in a grid-like arrangement in the first lane 710, with four apertures 712 aligned in rows across the width of the first lane 710 in the cross direction CD, and many apertures 712 aligned in four columns in the machine direction MD. The width of the first lanes 710 in the cross direction CD is at least four times the width of one of the apertures 712 in the cross direction CD. The apertures 712 in the embodiment illustrated in FIG. 7A have a substantially square shape, but may have any suitable shape, such as rectangular, diamond, polygonal, circular, elliptical, etc. Each side of each aperture 712 may have a length between about 0.1 mm and about 10 mm. In an embodiment, each side of each aperture 712 may have a length of about 0.5 mm to about 2 mm. In an embodiment, each side of each aperture 712 may have a length of about 1 mm. Although all of the apertures 712 illustrated in FIG. 7A have the same shape and size, embodiments of the invention contemplate having apertures of different shapes and sizes. The illustrated embodiment is not intended to be limiting in any way. Each of the plurality of second lanes 720 is comprised of a solid section 724 of the forming structure 700 that is devoid of apertures and has a width in the cross direction of greater than twice the width of the apertures 712 in the first lanes 710. In the embodiment illustrated in FIG. 7A, the first lanes 710 are wider than the second lanes 720. In an embodiment, the first lanes 710 may have the same width as the second lanes 720. In an embodiment, the first lanes 710 may be narrower than the second lanes 720. As the polymer melt curtain 504 drapes onto the forming structure 700 and the forming structure 700 rotates across the vacuum slot 510, vacuum is pulled through the plurality of apertures 712 and causes the polymer to flow into the apertures 712 as the polymer solidifies to form three-dimensional apertures in the elastic web 520.

FIG. 7B is a schematic illustration of a portion of an apertured elastic film 750 formed by the forming structure 700 in the apparatus 500 of FIG. 5. As illustrated, the apertured elastic film 750 includes a plurality of first lanes 760 extending in the machine direction MD, and a plurality of second lanes 770 extending in the machine direction MD and alternating with the plurality of first lanes 760 in the cross direction CD. As illustrated, the plurality of first lanes 760 and the plurality of second lanes 770 are generally straight. Each of the plurality of first lanes 760 includes a plurality of three-dimensional apertures 762 in the same pattern as the plurality of apertures 712 in the forming structure 700 illustrated in FIG. 7A. Each of the plurality of second lanes 770 includes a solid piece of film 774 that is devoid of apertures and has a width in the cross direction CD of at least twice the width of the apertures 762 in the first lanes 760 in the cross direction CD.

FIG. 8A is a schematic illustration of a portion of a forming structure 800, which may be used as the forming structure 506 of the apparatus 500 of FIG. 5, according to an embodiment of the invention. As illustrated, the forming structure 800 has a pattern that includes a plurality of first lanes 810 that alternate with a plurality of second lanes 820 in the cross direction CD and extend in the machine direction MD around the circumference of the forming structure 800. In the illustrated embodiment, the plurality of first lanes 810 and the plurality of second lanes 820 are generally straight. In an embodiment, the plurality of first lanes 810 and the plurality of second lanes 820 may be wavy, similar to a pattern described below with respect to FIG. 10. Each of the plurality of first lanes 810 includes a plurality of apertures 812 that extend through the forming structure 800. As illustrated, the apertures 812 are arranged in the first lane 810 such that one row extending in the cross direction CD includes two apertures 812 and alternating rows in the cross direction CD include one aperture 812, whereby the width of the first lane 810 is at least three times the width of one of the apertures 812 in the cross direction CD, and many apertures 812 are aligned in three columns in the machine direction MD. The apertures 812 in the embodiment illustrated in FIG. 8A are elliptical in shape, with a major axis oriented parallel to the cross direction CD, but may have any suitable shape, such as rectangular, square, diamond, polygonal, circular, etc. Each aperture 812 has a minor diameter and/or major diameter in the range of between about 0.1 mm and about 10 mm, or between about 0.5 mm to about 2 mm. Each of the plurality of second lanes 820 is comprised of a solid section 824 of the forming structure 800. In the embodiment illustrated in FIG. 8A, the first lanes 810 have about the same width as the second lanes 820. In an embodiment, the first lanes 810 may be wider or narrower than the second lanes 820. As the polymer melt curtain 504 drapes onto the forming structure 800 and the forming structure 800 rotates across the vacuum slot 510, vacuum is pulled through the plurality of apertures 812 and causes the polymer to flow into the apertures 812 as the polymer solidifies to form three-dimensional apertures in the elastic web 520.

FIG. 8B is a schematic illustration of an apertured elastic film 850 formed on the forming structure 800 in the apparatus 500 of FIG. 5. As illustrated, the apertured elastic film 850 includes a plurality of first lanes 860 extending in the machine direction MD, and a plurality of second lanes 870 extending in the machine direction MD and alternating with the plurality of first lanes 860 in the cross direction CD. As illustrated, the plurality of first lanes 860 and the plurality of second lanes 870 are generally straight. Each of the plurality of first lanes 860 includes a plurality of three-dimensional apertures 862 in the same pattern as the plurality of apertures 812 in the forming structure 800 illustrated in FIG. 8A. Each of the plurality of second lanes 870 includes a solid piece of film 874 that is devoid of apertures and has a width in the cross direction CD of at least twice the width of one of the apertures 862 in the first lanes 860 in the cross direction CD.

FIG. 9 is a schematic illustration of a portion of a forming structure 900, which may be used as the forming structure 506 of the apparatus 500 of FIG. 5, according to an embodiment of the invention. As illustrated, the forming structure 900 has a pattern that includes a plurality of first lanes 910 that alternate with a plurality of second lanes 920 in the cross direction CD and extend in the machine direction MD around the circumference of the forming structure 900. The illustrated pattern may extend across the entire width of the forming structure 900 in the cross direction CD. Each of the plurality of first lanes 910 includes a mesh-like structure that defines a plurality of apertures 912 that extend through the forming structure 900. The majority of the apertures 912 in the embodiment illustrated in FIG. 9 are substantially square in shape and oriented on a 45° angle relative to the cross direction CD. Each side of each aperture 912 may have a length of between about 0.1 mm and about 10 mm. In an embodiment, each side of each aperture 912 may have a length of about 0.5 mm to about 2 mm. Each of the plurality of second lanes 920 is comprised of a solid section 924 of the forming structure 900 and has a width in the cross direction CD of greater than twice the width of one of the apertures 912 in the first lanes 910 in the cross direction CD. In the embodiment illustrated in FIG. 9, the first lanes 910 have a width about twice the width of the second lanes 920. As the polymer melt curtain 504 drapes into the forming structure 900 and the forming structure 900 rotates across the vacuum slot 510, vacuum is pulled through the plurality of apertures 912 and causes the polymer to flow into the apertures 912 as the polymer solidifies to form three-dimensional apertures in the elastic web 520.

FIG. 10 is a schematic illustration of a portion of a forming structure 1000, which may be used as the forming structure 506 of the apparatus 500 of FIG. 5, according to an embodiment of the invention. As illustrated, the forming structure 1000 has a pattern that includes a plurality of first lanes 1010 that alternate with a plurality of second lanes 1020 in the cross direction CD and extend in the machine direction MD around the circumference of the forming structure 1000. The illustrated pattern may extend across the entire width of the forming structure 1000 in the cross direction CD. As illustrated in FIG. 10, the first lanes 1010 and the second lanes 1020 are in a wavy pattern. Each of the plurality of first lanes 1010 includes a mesh-like structure that defines a plurality of apertures 1012 that extend through the forming structure 1000. The majority of the apertures 1012 in the embodiment illustrated in FIG. 10 are substantially square in shape and oriented on a 45° angle relative to the cross direction CD. Each side of each aperture 1012 may have a length of between about 0.1 mm and about 10 mm. In an embodiment, each side of each aperture 1012 may have a length of about 0.5 mm to about 2 mm. Each of the plurality of second lanes 1020 is comprised of a solid section 1024 of the forming structure 1000 and has a width of greater than twice the width of one of the apertures 1012 in the first lanes 1010. In the embodiment illustrated in FIG. 10 the first lanes 1010 have a width slightly greater than the width of the second lanes 1020. As the polymer melt curtain 504 drapes onto the forming structure 1000 and the forming structure 1000 rotates across the vacuum slot 510, vacuum is pulled through the plurality of apertures 1012 and causes the polymer to flow into the apertures 1012 as the polymer solidifies to form three-dimensional apertures in the elastic web 520.

Figure 11:
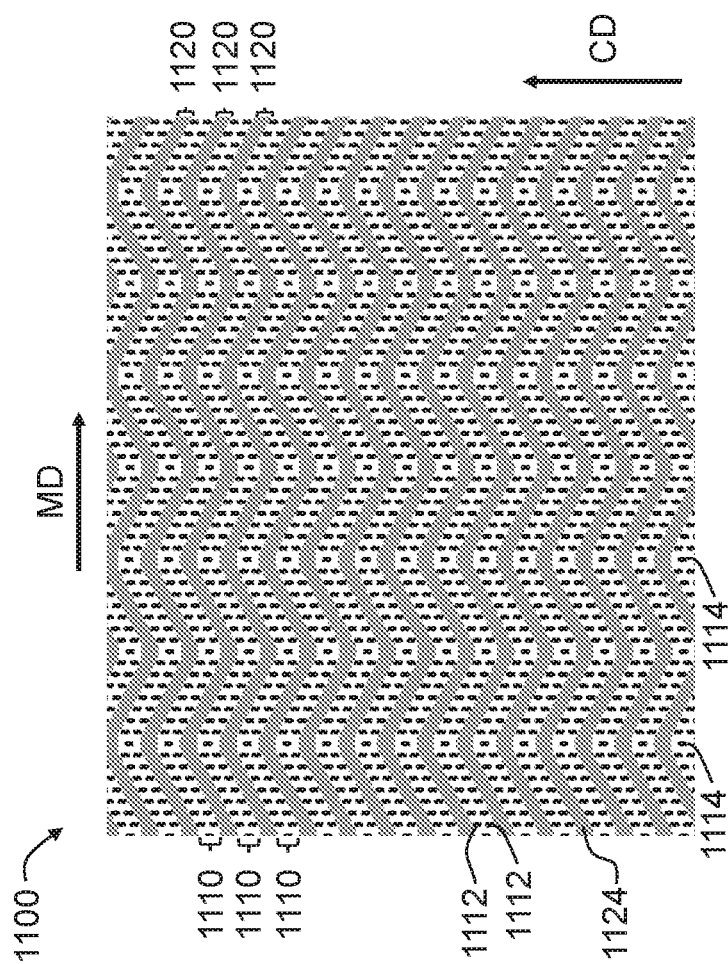
FIG. 11 is a schematic illustration of a portion of another embodiment of the forming structure of the apparatus of FIG. 5.

FIG. 11 is a schematic illustration of a portion of a forming structure 1100, which may be used as the forming structure 506 of the apparatus 500 of FIG. 5, according to an embodiment of the invention. As illustrated, the forming structure 1100 has a pattern that includes a plurality of first lanes 1110 that alternate with a plurality of second lanes 1120 in the cross direction CD and extend in the machine direction MD. As illustrated in FIG. 11, the first lanes 1110 and the second lanes 1120 are in a wavy or zig-zag pattern. Each of the plurality of first lanes 1110 includes a plurality of apertures 1112 that are arranged in pairs along each of the plurality of first lanes 1110, and a plurality of apertures 1114 that are arranged with one aperture 1114 at each inflection point of the wavy pattern. Each of the apertures 1112, 1114 extends through the forming structure 1100. The apertures 1112, 1114 in the embodiment illustrated in FIG. 10 are substantially rectangular in shape. Each side of each aperture 1112, 1114 may have a length of between about 0.1 mm and about 10 mm. In an embodiment, each side of each aperture 1112, 1114 may have a length of about 0.5 mm to about 2 mm. Each of the plurality of second lanes 1120 is comprised of a solid section 1124 of the forming structure 1100. In the embodiment illustrated in FIG. 11 the first lanes 1110 have a width slightly greater than the width of the second lanes 1120. As the polymer melt curtain 504 drapes onto the forming structure 1100 and the forming structure 1100 rotates across the vacuum slot 510, vacuum is pulled through the plurality of apertures 1112, 1114 and causes the polymer to flow into the apertures 1112, 1114 as the polymer solidifies to form three-dimensional apertures in the elastic web 520.

Figure 12:
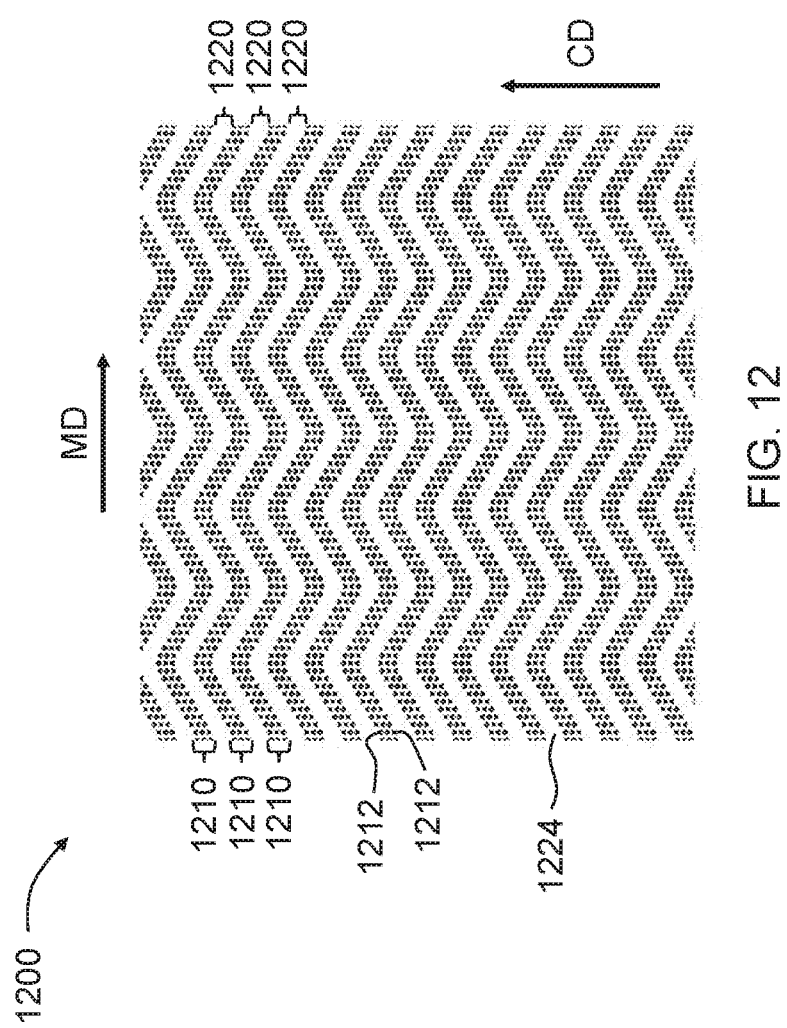
FIG. 12 is a schematic illustration of a portion of an apertured elastic film made on the apparatus of FIG. 5, according to an embodiment of the invention.

FIG. 12 illustrates a portion of an embodiment of an apertured elastic film 1200 that may be manufactured on the apparatus 500 with the forming structure 506 having a pattern similar to the pattern illustrated in FIG. 10. As illustrated in FIG. 12, the apertured elastic film 1200 includes a wavy pattern that includes a plurality of first lanes 1210 that alternate with a plurality of second lanes 1220 in the cross direction CD and extend in the machine direction MD. Each of the first lanes 1210 includes a plurality of three-dimensional apertures 1212, and each of the second lanes 1220 includes a solid portion 1224 of the film 1200 that is devoid of apertures. As illustrated, each of the second lanes 1220 has a width at least twice the width of one of the apertures 1212 in the first lanes 1210.

The illustrated embodiments of the various patterns for the forming structure 506 described above should not be considered to be limiting in any way. To the contrary, as would be appreciated by one of ordinary skill in the art, different combinations of features illustrated in FIGS. 7A, 8A and 9-11, including, for example, size and shape of the apertures, size and shape of the lanes, may be used to create a pattern that will form an apertured elastic film having the desired breathability and elastic properties.

Figure 13:
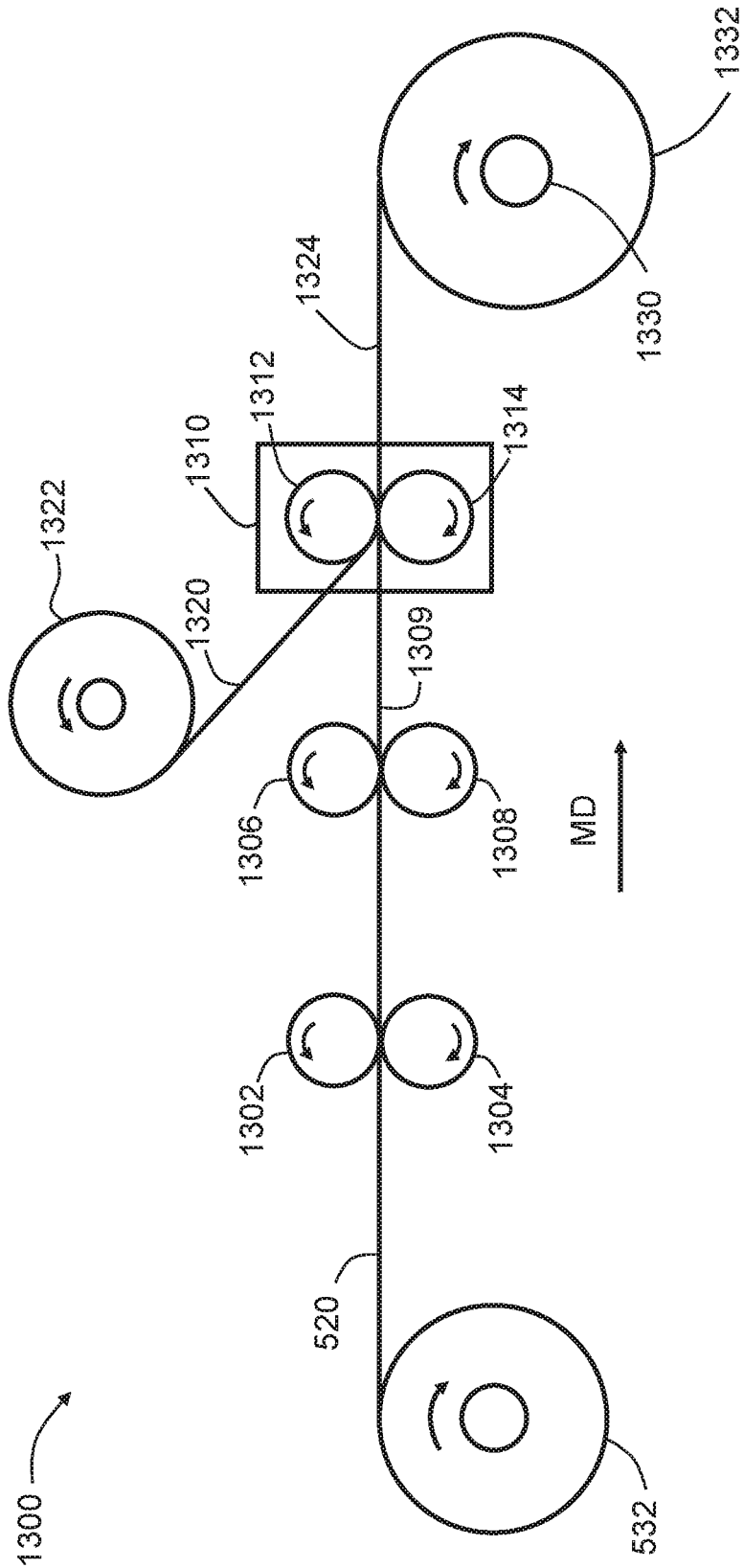
FIG. 13 is a schematic illustration of an apparatus for manufacturing breathable elastic laminates, according to embodiments of the invention.

FIG. 13 is a schematic illustration of an apparatus 1300 for manufacturing breathable elastic laminates 100 according to embodiments of the invention. As illustrated, the roll 532 of apertured elastic web 520 that was manufactured with the apparatus 500 of FIG. 5 is unwound and fed in the machine direction MD between a first roller 1302 and a second roller 1304, and then in between a third roller 1306 and a fourth roller 1308. The third roller 1306 and the fourth roller 1308 may rotate at speeds greater than the rotational speeds of the first roller 1302 and the second roller 1304 so that the apertured elastic web 520 is stretched and activated in the machine direction MD to create an activated apertured elastic web 1309 prior to being fed into a bonding station 1310. In an embodiment, the speeds of the various rollers 1302, 1304, 1306, 1308 may be adjusted so that the apertured elastic web 520 is stretched between 50% and 700% of a unit length of the apertured elastic web 520 in the machine direction MD. In an embodiment, the speeds of the various rollers 1302, 1304, 1306, 1308 may be adjusted so that the apertured elastic web 520 is stretched between 100% and 500% of a unit length of the apertured elastic web 520 in the machine direction MD. Additional rollers may be used to incrementally stretch the apertured elastic web 520 in the machine direction MD.

The bonding station 1310 includes a first bonding roller 1312 and a second bonding roller 1314. The first bonding roller 1312 and the second bonding roller 1314 may rotate at speeds that are sufficient to keep the activated apertured web 1309 under tension. In an embodiment, the first bonding roller 1312 and the second bonding roller 1314 may rotate at slightly slower than the speeds of the third roller 1306 and the fourth roller 1308 to allow the activated apertured elastic web 1309 to relax and have a reduction in unit length by at least 5% prior to passing between the first bonding roller 1312 and the second bonding roller 1314, while still keeping the activated apertured elastic web 1309 under tension. In an embodiment, the activated apertured elastic web 1309 may be relaxed to have a reduction in unit length by between 5% and 70%. In an embodiment, the activated apertured elastic web 1309 may be relaxed to have a reduction in unit length by between 10% and 40%. In an embodiment, additional rollers located upstream of the bonding station 1310, but downstream of the rollers 1306, 1308 may be used to relax the activated apertured elastic web 1309 prior to entering the bonding station 1310.

A nonwoven web 1320 is unwound from a roll 1322 and also fed into the bonding station 1310 where it is bonded to the activated apertured elastic web 1309 held under tension to create a breathable elastic laminate 1324, which may be wound by a winder 1330 into a roll 1332. In an embodiment, the nonwoven web 1320 may have a basis weight in the range of about 5 gsm to about 50 gsm. In an embodiment, the basis weight of the nonwoven web 1320 may be in the range of about 8 gsm to about 20 gsm. The nonwoven web 1320 may include a nonwoven material selected from the group consisting of a spunbond nonwoven material, a spunlace nonwoven material, a spunbond-meltblown-spunbond ("SMS") nonwoven material, and a spunbond-meltblown-meltblown-spunbond ("SMMS") nonwoven material.

In an embodiment, the nonwoven web 1320 may be under a predetermined level of tension as it is fed into the bonding station 1310. In an embodiment, the bonding station 1310 may be configured to perform a point bonding operation on the activated apertured elastic web 1309 and the nonwoven web 1320. In an embodiment, the bonding station 1310 may be configured to perform a sonic bonding operation on the activated apertured elastic web 1309 and the nonwoven web 1320. Desirably, the bonding operation performed by the bonding station 1310 does not create additional apertures in the activated apertured elastic web 1309.

Figure 14:
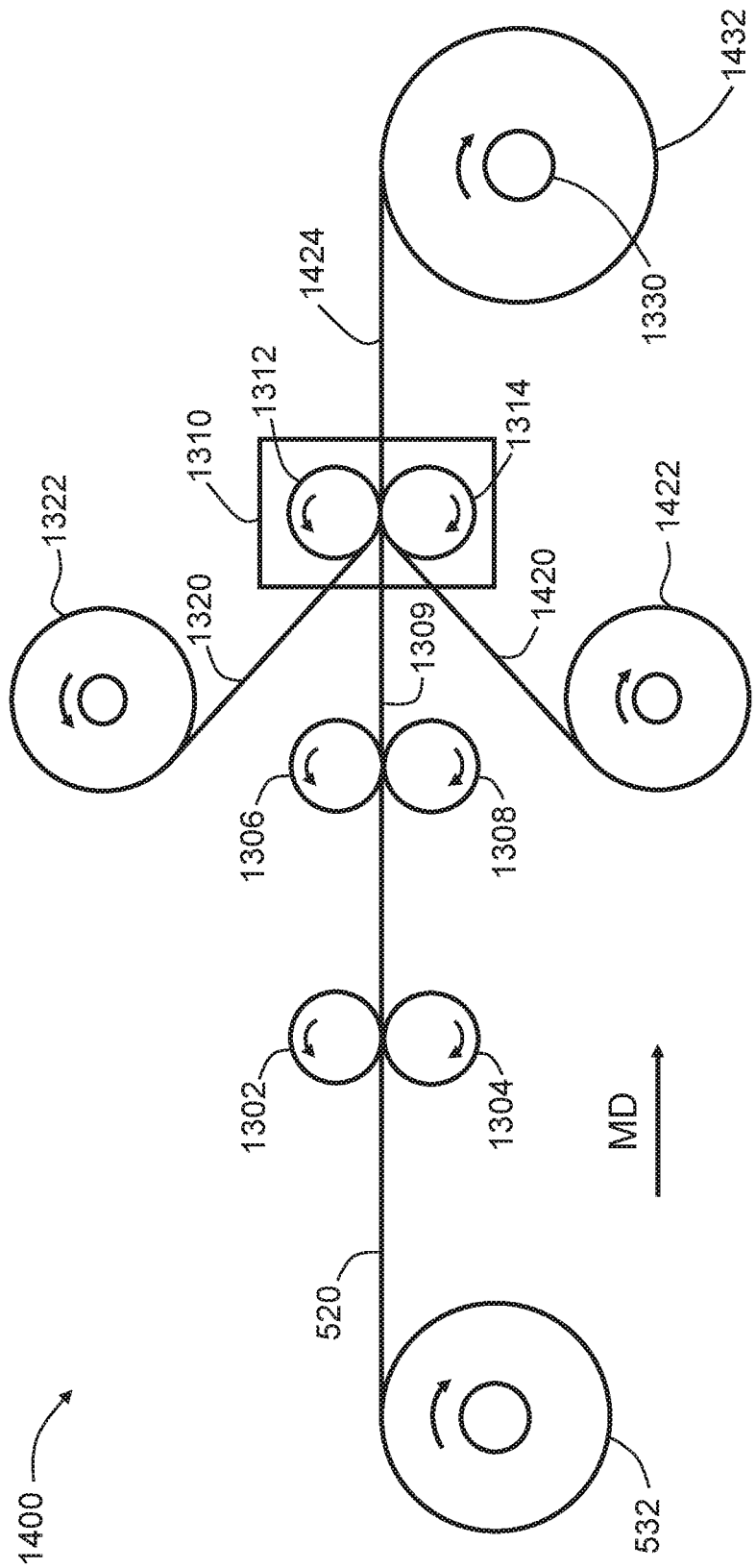
FIG. 14 is a schematic illustration of an apparatus for manufacturing breathable elastic laminates, according to embodiments of the invention.

FIG. 14 is a schematic illustration of an apparatus 1400 for manufacturing breathable elastic laminates 200 according to embodiments of the invention. The apparatus 1400 has many of the same parts as the apparatus 1300 of FIG. 13, and also includes a second nonwoven web 1420 that is unwound from a roll 1422 and also fed into the bonding station 1310 on a side of the activated apertured elastic web 1309 that is opposite the nonwoven web 1320. In an embodiment, the second nonwoven web 1420 may have a basis weight in the range of about 5 gsm to about 50 gsm. In an embodiment, the basis weight of the second nonwoven web 1420 may be in the range of about 8 gsm to about 20 gsm. The nonwoven web 1420 may include a nonwoven material selected from the group consisting of a spunbond nonwoven material, a spunlace nonwoven material, a spunbond-meltblown-spunbond ("SMS") nonwoven material, and a spunbond-meltblown-meltblown-spunbond ("SMMS") nonwoven material. The nonwoven material of the second nonwoven web 1420 may be the same as or different from the nonwoven material of the nonwoven web 1320.

In an embodiment, the second nonwoven web 1420 may be under a predetermined level of tension as it is fed into the bonding station 1310. A breathable elastic laminate 1424, which is a nonwoven/film/nonwoven trilaminate, exits the bonding station 1310 and is wound by the winder 1330 into a roll 1432.

Figure 15:
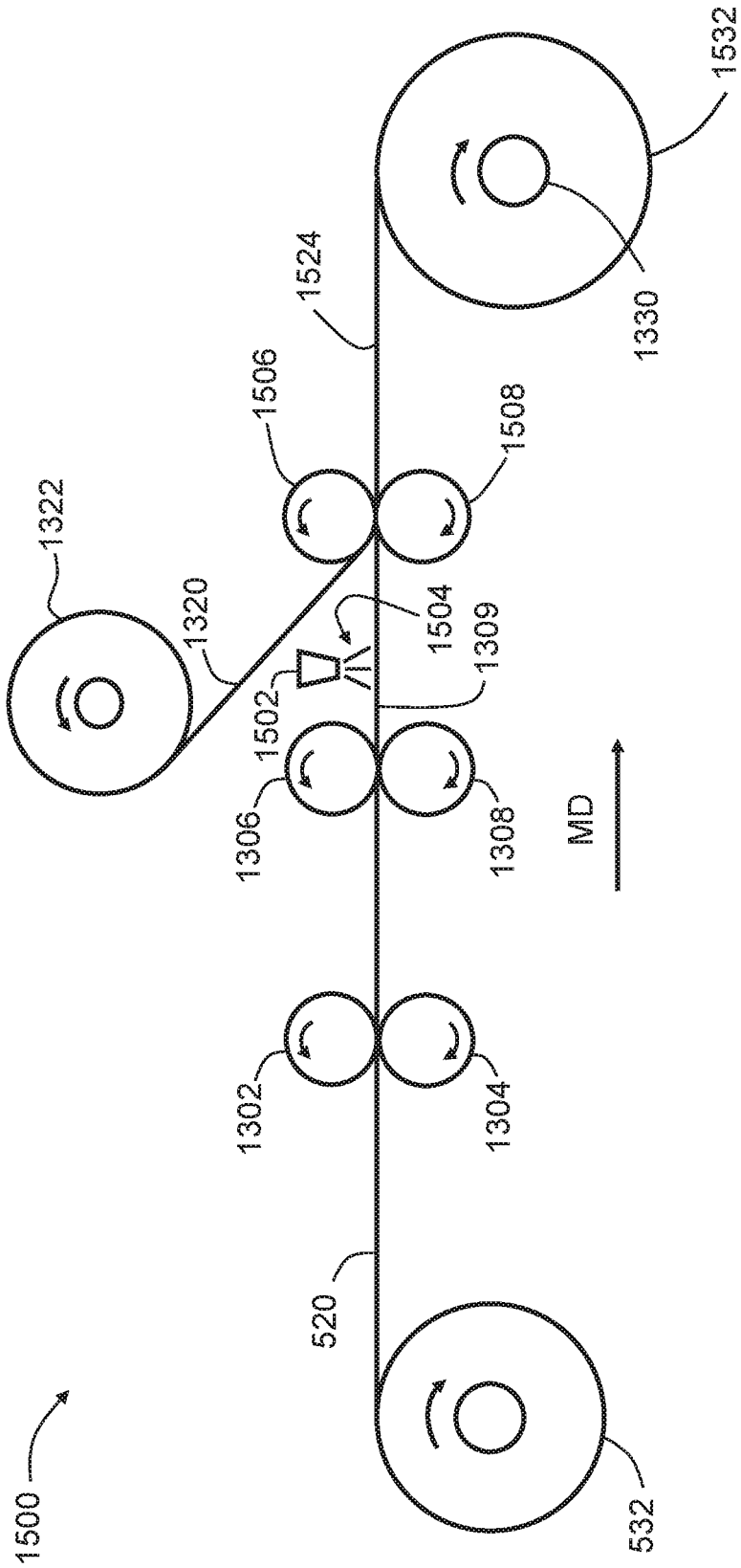
FIG. 15 is a schematic illustration of an apparatus for manufacturing breathable elastic laminates, according to embodiments of the invention.

FIG. 15 is a schematic illustration of an apparatus 1500 for manufacturing breathable elastic laminates 100 according to embodiments of the invention. The apparatus 1500 has many of the same parts as the apparatus 1300 illustrated in FIG. 13 with a few notable differences. For example, in place of the bonding station 1310, an adhesive applicator 1502 provides an adhesive 1504 to the activated apertured elastic web 1309 prior to being fed between a first bonding roller 1506 and a second bonding roller 1508. The first bonding roller 1506 and the second bonding roller 1508 may rotate at speeds that are sufficient to keep the activated apertured web 1309 under tension. In an embodiment, the first bonding roller 1506 and the second bonding roller 1508 may rotate at slightly slower than the speeds of the third roller 1306 and the fourth roller 1308 to allow the activated apertured elastic web 1309 to relax and have a reduction in unit length by at least 5% prior to passing between the first bonding roller 1506 and the second bonding roller 1508, while still keeping the activated apertured elastic web 1309 under tension. In an embodiment, the activated apertured elastic web 1309 may be relaxed to have a reduction in unit length by between 5% and 70%. In an embodiment, the activated apertured elastic web 1309 may be relaxed to have a reduction in unit length by between 10% and 40%. In an embodiment, additional rollers located upstream of the bonding rollers 1506, 1508, but downstream of the rollers 1306, 1308 may be used to relax the activated apertured elastic web 1309 prior to the activated apertured elastic web 1309 receiving the adhesive 1504 from the adhesive applicator 1502.

The nonwoven web 1320 is also fed between the first bonding roller 1506 and the second bonding roller 1508. The first bonding roller 1506 and the second bonding roller 1508 apply a suitable pressure to the activated apertured elastic web 1309 and the nonwoven web 1320 to create a breathable elastic laminate 1524 in the form of a bi-laminate, which may be wound by the winder into a roll 1532. In an embodiment, the adhesive 1504 may be applied directly to the nonwoven web 1320 instead of or in addition to the activated apertured elastic web 1309. The illustrated embodiment is not intended to be limiting in any way.

Figure 16:
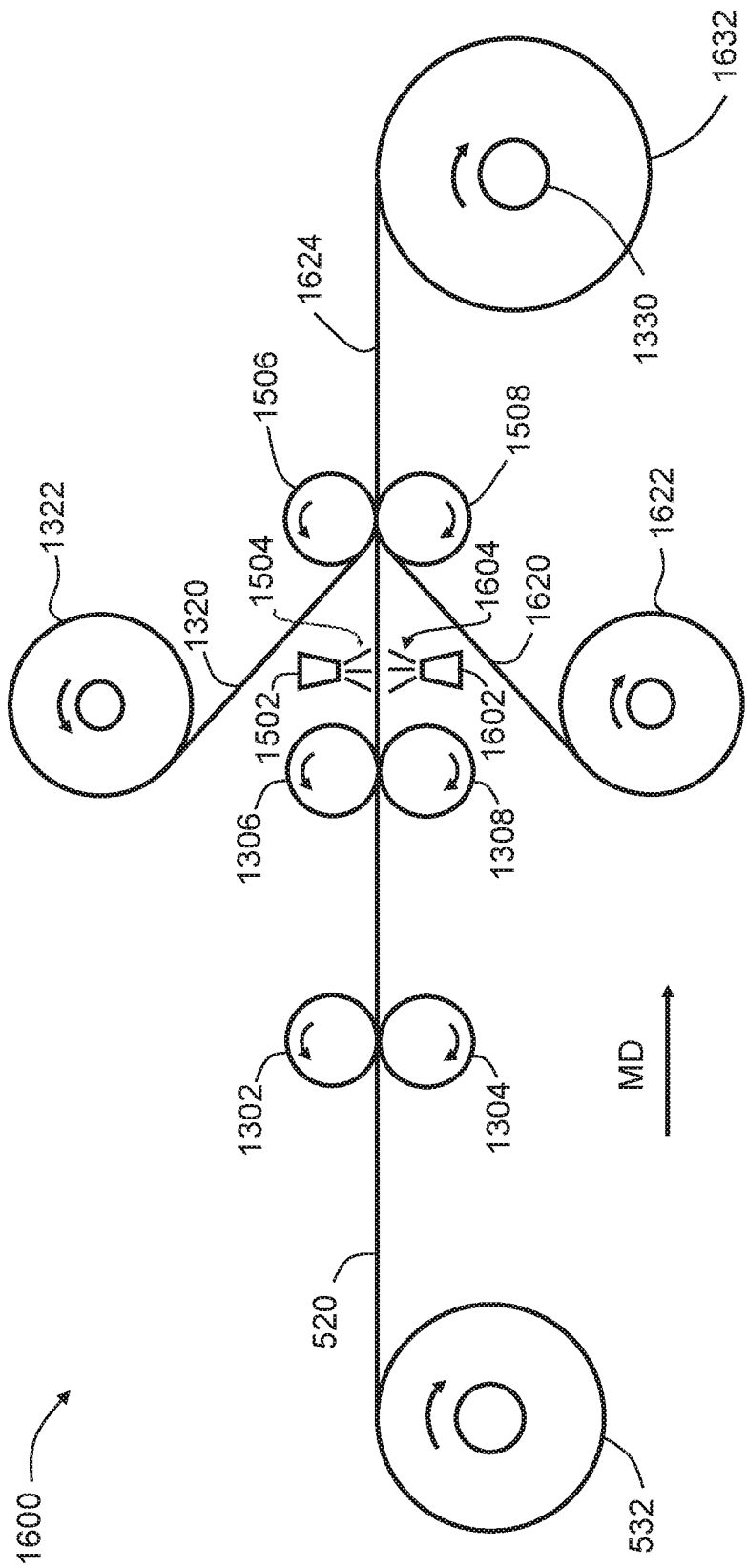
FIG. 16 is a schematic illustration of an apparatus for manufacturing breathable elastic laminates, according to embodiments of the invention.

FIG. 16 is a schematic illustration of an apparatus 1600 for manufacturing breathable elastic laminates according to embodiments of the invention. The apparatus 1600 has the same parts as the apparatus 1500 illustrated in FIG. 15, and also includes a second adhesive applicator 1602 that provides an adhesive 1604 to the other side of the activated apertured elastic web 1309 prior to being fed between the first bonding roller 1506 and the second bonding roller 1508. The nonwoven web 1320, as well as a second nonwoven web 1620 that is unwound from a roll 1622, are also fed between the first bonding roller 1506 and the second bonding roller 1508. In an embodiment, the second nonwoven web 1620 may have a basis weight in the range of about 5 gsm to about 50 gsm. In an embodiment, the basis weight of the second nonwoven web 1620 may be in the range of about 8 gsm to about 20 gsm. The second nonwoven web 1620 may include a nonwoven material selected from the group consisting of a spunbond nonwoven material, a spunlace nonwoven material, a spunbond-meltblown-spunbond ("SMS") nonwoven material, and a spunbond-meltblown-meltblown-spunbond ("SMMS") nonwoven material. The nonwoven material of the second nonwoven web 1620 may be the same as or different from the nonwoven material of the nonwoven web 1320.

In an embodiment, the second nonwoven web 1620 may be under a predetermined level of tension as it is fed between the first bonding roller 1506 and the second bonding roller 1508. The first bonding roller 1506 and the second bonding roller 1508 apply a suitable pressure to the nonwoven web 1320, the activated apertured elastic web 1309, and the second nonwoven web 1620 to create a breathable elastic laminate 1624 in the form of a tri-laminate, which may be wound by the winder 1330 into a roll 1632. In an embodiment, the adhesive 1504 may be applied directly to the nonwoven web 1320, and/or the adhesive 1604 may be applied directly to the second nonwoven web 1620 instead of or in addition to the activated apertured elastic web 1309. The illustrated embodiment is not intended to be limiting in any way.

For example, in an embodiment, the apparatus 500 of FIG. 5 and any of the apparatus 1300, 1400, 1500, 1600 of FIGS. 13-16 may be combined so that the apertured elastic film 520 is created in-line, instead of being wound into a roll 532 and then unwound prior to lamination.

The breathable elastic laminates 1324, 1424, 1524, 1624 according to embodiments of the invention may have air permeabilities between about 0.1 $m^3/m^2$/minute and about 150 $m^3/m^2$/minute when measured in a device such as a Textest FX3300 Air Permeability Tester. In some embodiments, the breathable elastic laminates 1324, 1424, 1524, 1624 may have air permeabilities between about 10 $m^3/m^2$/minute and about 50 $m^3/m^2$/minute.

FIG. 17 is a flow chart for a method 1700 for manufacturing a breathable elastic laminate, such as the breathable elastic laminates 100, 200, 300 described above. The method starts at 1710. At 1720, an elastic polymer film is apertured.

At 1730, the apertured elastic polymer film is activated in the machine direction MD by stretching the apertured elastic polymer film between 50% and 700% of a unit length of the apertured elastic polymer film in the machine direction MD. In an embodiment, the apertured elastic polymer film may be stretched between 100% and 500% of a unit length of the apertured elastic polymer film in the machine direction MD. At 1740, the activated apertured elastic polymer film is optionally relaxed by at least 5% while being kept under tension. In an embodiment, the activated apertured elastic polymer film may be relaxed by between 5% and 70%. In an embodiment, the activated apertured elastic polymer film may be relaxed by between 10% and 40%. At 1750, the activated apertured elastic polymer film is bonded to at least one nonwoven web to form a breathable elastic laminate. The method ends at 1760.

Figure 18:
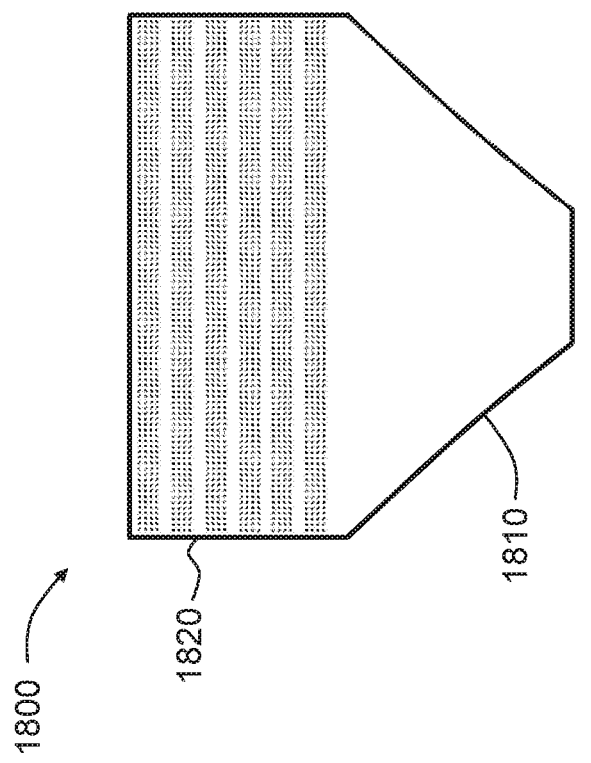
FIG. 18 is a schematic illustration of an absorbent article that includes a breathable elastic laminate, according to embodiments of the invention.

FIG. 18 is a schematic illustration of an absorbent article 1800 according to an embodiment of the invention. The absorbent article 1800 may be, for example, a pull-up diaper or training pants for a child, or an adult incontinence brief for an adult. The absorbent article includes a main chassis 1810 that includes an absorbent core, for example, and an upper portion 1820 that includes the breathable elastic laminate according to embodiments of the invention described above. Although the pattern of the apertures in the apertured elastic web are illustrated in order to illustrate the orientation of the breathable elastic laminate, the pattern of apertures in the apertured elastic web may not be visible due to the presence of a nonwoven web bonded to the apertured elastic web.

Figure 19:
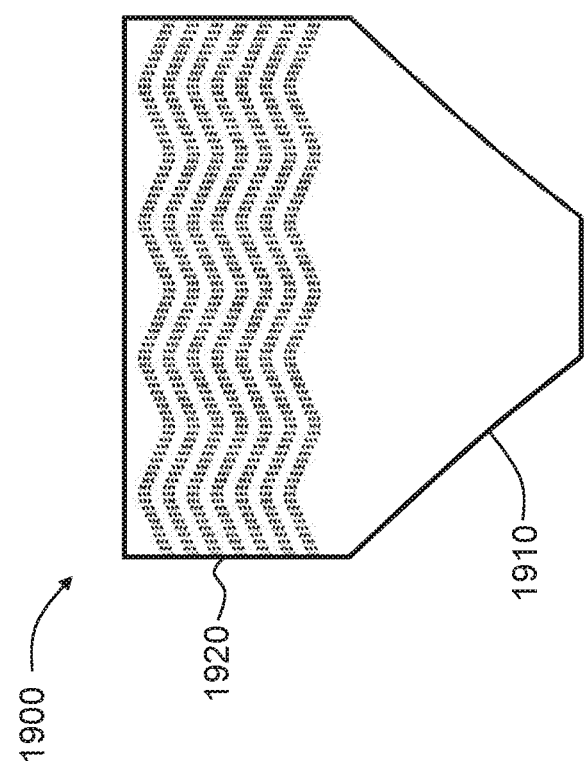
FIG. 19 is a schematic illustration of an absorbent article that includes a breathable elastic laminate, according to embodiments of the invention.

FIG. 19 is a schematic illustration of an absorbent article 1900 according to an embodiment of the invention. Like the absorbent article 1800 of FIG. 18, the absorbent article 1900 may be, for example, a pull-up diaper or training pants for a child, or an adult incontinence brief for an adult. The absorbent article 1900 includes a main chassis 1910 that includes an absorbent core, for example, and an upper portion 1920 that includes the breathable elastic laminate according to embodiments of the invention described above. Although the pattern of the apertures in the apertured elastic web are illustrated in order to illustrate the orientation of the breathable elastic laminate, the pattern of apertures in the apertured elastic web may not be visible due to the presence of a nonwoven web bonded to the apertured elastic web.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A method for manufacturing a breathable elastic laminate, the method comprising:
   aperturing an elastic film to create an apertured elastic film with a pattern, the pattern comprising
   a plurality of first lanes extending in a machine direction, each of the plurality of first lanes comprising a plurality of apertures, and
   a plurality of second lanes extending in the machine direction, each of the plurality of second lanes devoid of apertures and having a width greater than twice the width of one of the plurality of apertures in the first lanes,
   the plurality of second lanes alternating with the plurality of first lanes in a cross direction substantially orthogonal to the machine direction;
   stretching the apertured elastic film in the machine direction to activate the apertured elastic film in the machine direction; and
   bonding a first side of the activated apertured elastic film with the activated apertured elastic film under tension to a nonwoven web to create a breathable elastic laminate, after the elastic film is apertured,
   wherein the plurality of apertures are three-dimensional apertures.

2. The method according to claim 1, further comprising relaxing the activated apertured elastic film prior to bonding.

3. The method according to claim 2, wherein the activated apertured elastic film is relaxed at least 5%.

4. The method according to claim 3, wherein the activated apertured elastic film is relaxed between 5% and 70%.

5. The method according to claim 4, wherein the activated apertured elastic film is relaxed between 10% and 40%.

6. The method according to claim 1, wherein the elastic film is apertured using an apertured forming structure and a vacuum.

7. The method according to claim 1, further comprising activating the apertured elastic film in the cross direction prior to stretching the apertured elastic film in the machine direction.

8. The method according to claim 1, wherein said bonding comprises sonic bonding.

9. The method according to claim 1, wherein said bonding comprises applying an adhesive to the apertured elastic film or the nonwoven web.

10. The method according to claim 1, further comprising bonding a second side of the apertured elastic film, opposite the first side, to a second nonwoven web.

11. The method according to claim 1, wherein the apertured elastic film is stretched up to 400% in the machine direction.

12. A breathable elastic laminate comprising:
   an apertured elastic film layer having a pattern, the pattern comprising
   a plurality of first lanes extending in a machine direction, each of the plurality of first lanes comprising a plurality of apertures, and
   a plurality of second lanes extending in the machine direction, each of the plurality of second lanes devoid of apertures and having a width at least twice the width of one of the plurality of apertures in the first lanes,
   the plurality of second lanes alternating with the plurality of first lanes in a cross direction substantially orthogonal to the machine direction; and
   a nonwoven layer attached to a first surface of the apertured elastic film layer,
   wherein the apertured elastic film is stretched in at least one of the machine direction and the cross direction to activate the elastic film in the at least one of the machine direction and the cross direction,
   wherein a first side of the activated apertured elastic film is bonded to the nonwoven web while the apertured elastic film is under tension,
   wherein the plurality of apertures is formed in the apertured elastic film before the apertured elastic film is bonded to the nonwoven web, and wherein the plurality of apertures are three-dimensional apertures.

13. The breathable elastic laminate according to claim 12, further comprising a second nonwoven layer attached to a second surface of the elastic film layer, opposite the first surface.

14. The breathable elastic laminate according to claim 12, wherein the breathable elastic laminate has an air permeability between about 0.1 m$^3$/m$^2$/minute and about 150 m$^3$/m$^2$/minute.

15. The breathable elastic laminate according to claim 14, wherein the breathable elastic laminate has an air permeability between about 10 m$^3$/m$^2$/minute and about 50 m$^3$/m$^2$/minute.

16. The breathable elastic laminate according to claim 12, wherein the apertured film layer has a basis weight between about 5 gsm and about 50 gsm.

17. The breathable elastic laminate according to claim 16, wherein the apertured film layer has a basis weight between about 25 gsm and about 40 gsm.

18. The breathable elastic laminate according to claim 12, wherein the nonwoven layer comprises a nonwoven material having a basis weight between about 10 gsm and about 50 gsm.

19. The breathable elastic laminate according to claim 18, wherein the nonwoven material has a basis weight between about 20 gsm and about 40 gsm.

20. The breathable elastic laminate according to claim 12, wherein the nonwoven layer comprises a nonwoven material selected from the group consisting of a spunbond nonwoven material, a spunlace nonwoven material, a spunbond-meltblown-spunbond ("SMS") nonwoven material, and a spunbond-meltblown-meltblown-spunbond ("SMMS") nonwoven material.

21. The breathable elastic laminate according to claim 12, wherein the plurality of first lanes and the plurality of second lanes are generally straight.

22. The breathable elastic laminate according to claim 12, wherein the plurality of first lanes and the plurality of second lanes are wavy.

23. The breathable elastic laminate according to claim 12, wherein apertures in addition to the plurality of apertures are not created when the apertured elastic film is bonded to the nonwoven web.

24. An absorbent article comprising:

a breathable elastic laminate comprising an apertured elastic film layer having a pattern, the pattern comprising a plurality of first lanes extending in a machine direction, each of the plurality of first lanes comprising a plurality of apertures, and a plurality of second lanes extending in the machine direction, each of the plurality of second lanes devoid of apertures and having a width at least twice the width of one of the plurality of apertures in the first lanes, the plurality of second lanes alternating with the plurality of first lanes in a cross direction substantially orthogonal to the machine direction; and a nonwoven layer attached to a first surface of the apertured elastic film layer, wherein the apertured elastic film is stretched in at least one of the machine direction and the cross direction to activate the elastic film in the at least one of the machine direction and the cross direction, wherein a first side of the activated apertured elastic film is bonded to the nonwoven web while the apertured elastic film is under tension, and wherein the plurality of apertures is formed in the apertured elastic film before the apertured elastic film is bonded to the nonwoven web, and wherein the plurality of apertures are three-dimensional apertures.

25. The absorbent article of claim 24, wherein apertures in addition to the plurality of apertures are not created when the apertured elastic film is bonded to the nonwoven web.

* * * * *